United States Patent
Markkula et al.

(10) Patent No.: US 6,299,894 B1
(45) Date of Patent: *Oct. 9, 2001

(54) DRUG DELIVERY DEVICE, ESPECIALLY FOR THE DELIVERY OF GESTODENE

(75) Inventors: Tommi Markkula, Sale (GB); Juha Ala-Sorvari; Harri Jukarainen, both of Turku (FI); Matti Lehtinen, Piispanristi (FI); Jarkko Ruohonen, Vanhalinna (FI)

(73) Assignee: Leiras Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,027

(22) Filed: May 10, 2000

(51) Int. Cl.⁷ ..................................... A61F 13/00
(52) U.S. Cl. .................. 424/422; 424/449; 424/430; 424/486; 424/473
(58) Field of Search .................... 424/422, 473, 424/486, 449, 430

(56) References Cited

U.S. PATENT DOCUMENTS

| | | |
|---|---|---|
| 6,056,976 | 5/2000 | Markkula et la. ............. 424/486 |
| 6,063,395 | 5/2000 | Markkula et al. ............. 424/422 |

OTHER PUBLICATIONS

Sun et al., "Effect of Polymer Composition on Steroid Permeation: Membrane Permeation Kinetics of Androgens and Progestrins," 5 *J. Controlled Release* 69–78 (1987).

Gaginella et al., "Nicotine Base Permeation Through Silicone Elastomers: Comparison of Dimethylpolysiloxane and Trifluoropropylmethylpolysiloxane Systems," 63 *J. Pharm. Sci.* 1849 (1974).

*Primary Examiner*—Thurman K. Page
*Assistant Examiner*—Robert M. Joynes
(74) *Attorney, Agent, or Firm*—James C. Lydon

(57) ABSTRACT

The invention relates to a delivery device for the controlled release of the therapeutically active agent gestodene, over a prolonged period of time, at a release rate of 0,1–300 μg/day, said device comprising a core comprising at least said therapeutically active agent, and a membrane encasing said core wherein said membrane is made of an elastomer. According to the invention, the elastomer is a siloxane-based elastomer comprising 3,3,3-trifluoropropyl groups attached to the Si-atoms of the siloxane units, and the release rate of said therapeutically active agent of said delivery device is regulated by the amount of said 3,3,3-trifluoropropyl groups.

12 Claims, 1 Drawing Sheet

DRUG DELIVERY DEVICE, ESPECIALLY FOR THE DELIVERY OF GESTODENE

FIELD OF THE INVENTION

Figure 1:
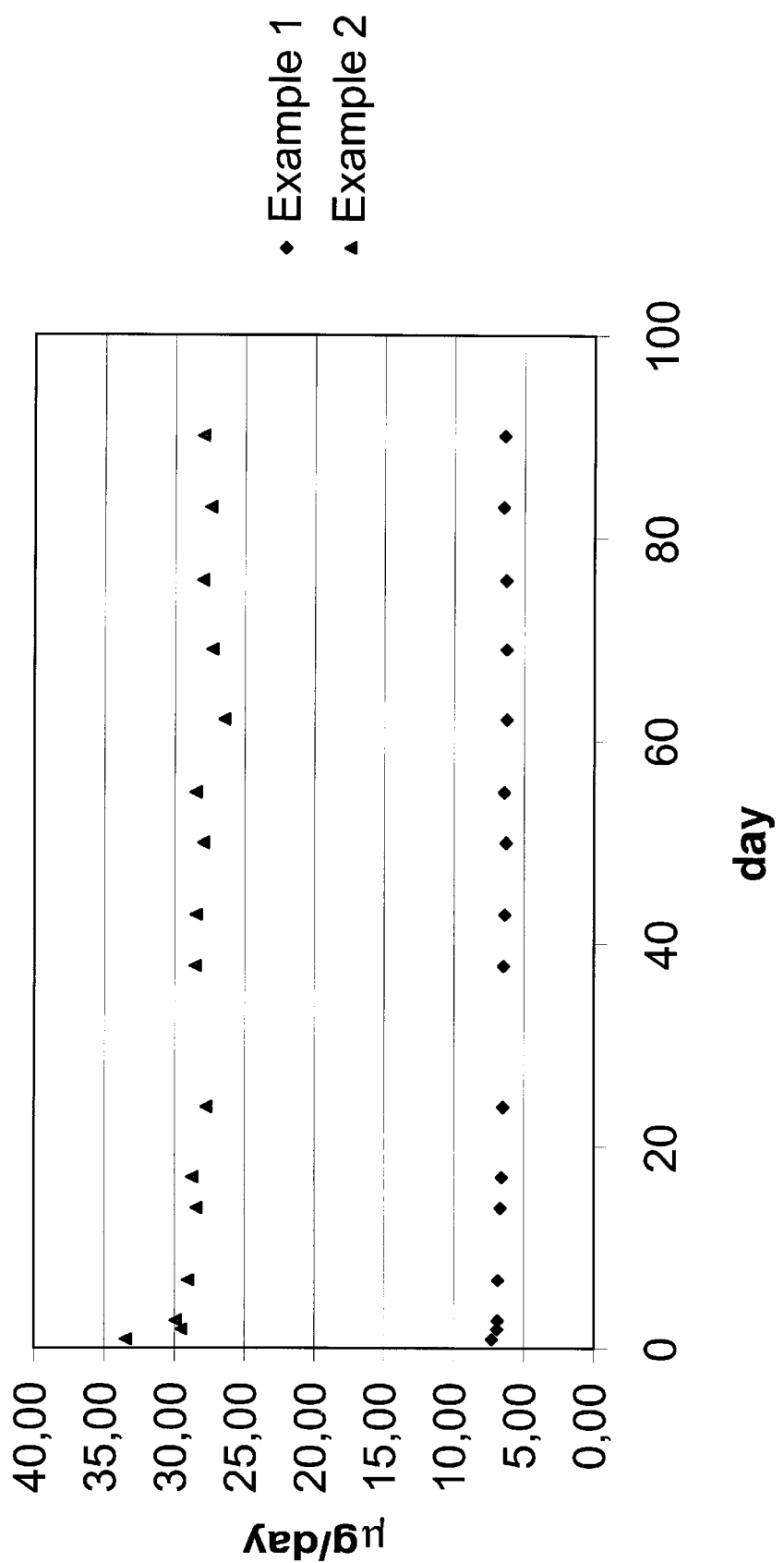

This invention relates to a drug delivery device, particularly to a device intended for administration of gestodene, at a substantially constant rate for a prolonged period of time.

BACKGROUND OF THE INVENTION

The publications and other materials used herein to illuminate the background of the invention, and in particular, the cases to provide additional details respecting the practice, are incorporated by reference.

Polysiloxanes, such as poly(dimethylsiloxane) (PDMS), are highly suitable for use as a membrane or a matrix regulating the permeation of drugs in various drug forms, in particular in implants and intra-uterine systems (IUS). Polysiloxanes are physiologically inert, and a wide group of drugs are capable of penetrating polysiloxane membranes, which also have the required mechanical properties.

It is known from the literature that the adding of poly (ethylene oxide) groups, i.e. PEO groups, to a PDMS polymer may increase the perneation of drugs. Publication KL Ullman et al., Journal of Controlled Release 10 (1989) 251–260, describes membranes prepared from a block copolymer which contains PEO and PDMS and the penetration of various steroids through these membranes. It is further known that membranes based on modified PDMS polymers, in which a certain amount of the methyl substituents at the Si-atoms are replaced by trifluoropropyl groups, decrease the permeation of drugs. The publication Ying Sun et al., Journal of Controlled Release, 5 (1987) 69–78, describes the effect on membranes prepared from PDMS, trifluoropropyl substituted PDMS and PDMS/PEO/PMMA (where PMMA is poly(methylmethacrylate)) on the permeation of androgenic and progestenic steroids. The study shows that the permeation for both groups of steroids was lower for the membrane made of trifluoropropyl substituted PDMS than for that made of unmodified PDMS. The publication does not, however, disclose any elastomer made of trifluoropropyl substituted PDMS.

OBJECTS AND SUMMARY OF THE INVENTION

The object of this invention is to provide a drug delivery device, particularly a device intended for administration of gestodene, at a substantially constant rate for a prolonged period of time.

The object is particularly to provide a device with which the drug release rate can easily be adjusted.

Thus, the invention concerns a delivery device for the controlled release of the therapeutically active agent gestodene, over a prolonged period of time, at a release rate of 0,1–300 μg/day, said device comprising a core comprising at least said therapeutically active agent, and a membrane encasing said core wherein said membrane is made of an elastomer.

According to the invention, the elastomer is a siloxane-based elastomer comprising 3,3,3-trifluoropropyl groups attached to the Si-atoms of the siloxane units, and the release rate of said therapeutically active agent of said delivery device is regulated by the amount of said 3,3,3-trifluoropropyl groups.

DETAILED DESCRIPTION OF THE INVENTION

The device according to the invention can for example be an implant, an intrauterine device, an intravaginal device or an intracervical device. According to one embodiment of the invention, the release rate of the active agent in an intrauterine device is 0,1–300 μg/day, preferably 0,5–100 μg/day, more preferably 0,5–50 μg/day and most preferably 0,5–30 μg/day. According to another embodiment of the invention, the release rate of the active agent in an implant is 0,1–300 μg/day, preferably 0,5–200 μg/day and more preferably 1–100 μg/day.

Description of the Elastomer

The elastomer suitable for use in the device according to this invention, particularly for use in the membrane of the device, is a siloxane-based elastomer comprising 3,3,3-trifluoropropyl groups attached to the Si-atoms of the siloxane units.

The term "siloxane-based elastomer" shall be understood to cover elastomers made of poly(disubstituted siloxanes) where the substituents mainly are lower alkyl, preferably alkyl groups of 1 to 6 carbon atoms, or phenyl groups, wherein said alkyl or phenyl can be substituted or unsubstituted. A widely used and preferred polymer of this kind is poly(dimethylsiloxane) (PDMS).

According to the invention, a certain amount of the substituents attached to the Si-atoms of the siloxane units in the elastomer shall be 3,3,3-trifluoropropyl groups. Such an elastomer can be achieved in different ways. According to one embodiment, the elastomer can be based on one single crosslinked siloxane-based polymer, such as a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) the structure of which is shown as Compound I below.

Compound I

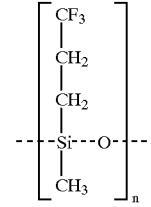

A polymer of this kind, in which approximately 50% of the methyl substituents at the Si-atoms are replaced by 3,3,3-trifluoropropyl groups, is commercially available. The term "approximately 50%" means that the degree of 3,3,3-trifluoropropyl substitution is in fact somewhat below 50%, because the polymer must contain a certain amount (about 0.15% of the substituents) of crosslinkable groups such as vinyl or vinyl-terminated groups. Similar polymers having lower substitution degree of 3,3,3-trifluoropropyl groups can easily be synthetised.

The retarding effect of the 3,3,3-trifluoropropyl groups on the permeation of drugs across a membrane of the elastomer is dependent on the amount of these groups. Furthermore, the effect is highly dependent on the drug used. If the elastomer is made of one single polymer only, it would be necessary to prepare and use polymers with different amounts of 3,3,3-trifluoropropyl groups for different drugs.

According to another embodiment, which is particularly preferred if suitable elastomers for several different drugs are needed, is to crosslink a mixture comprising a) a non-fluorosubstituted siloxane-based polymer and b) a fluorosubstituted siloxane-based polymer, where said polymer comprises 3,3,3-trifluoropropyl groups attached to the Si-atoms of the siloxane units. The first ingredient of the mixture, the non-fluorosubstituted polymer, can be any poly(disubstituted siloxane) where the substituents mainly are lower alkyl, preferably alkyl groups of 1 to 6 carbon atoms, or phenyl groups, wherein said alkyl or phenyl can be substituted or unsubstituted. The substituents are most preferably alkyl groups of 1 to 6 carbon atoms. A preferred nonfluorosubstituted polymer is PDMS. The second ingredient of the mixture, the fluoro-substituted polymer, can for example be a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) as mentioned above. A particularly preferable polymer of this kind is a polymer having as high amount of 3,3,3-trifluoropropyl substituents as possible, such as the commercially available polymer, in which approximately 50% of the methyl substituents at the Si-atoms are replaced by 3,3,3-trifluoropropyl groups. An elastomer with great permeation retarding effect can be achieved by using exclusively or mainly the aforementioned polymer. Elastomers with less retarding influence on the permeation of the drug can be obtained by using mixtures with increasing amounts of the non-fluorosubstituted siloxane-based polymer.

The elastomer should preferably comprise a filler, such as amorphous silica, in order to give a sufficient strength for the membrane made from said elastomer.

General Description of the Method for the Preparation of the Elastomer

According to one embodiment, the elastomer is prepared by crosslinking, in the presence of a catalyst, a vinyl-functional polysiloxane component and a silicon hydride-functional crosslinking agent.

By crosslinking is meant the addition reaction of the silicon hydride-functional crosslinkng agent with the carbon-carbon double bond of the vinyl-functional polysiloxane component.

According to another embodiment, the elastomer is prepared by crosslinking the polymer in the presence of a peroxide catalyst.

The term "vinyl-functional" polysiloxane shall be understood to cover polysiloxanes substituted with vinyl groups or with vinyl-terminated groups. The "vinyl-functional polysiloxane component" and the "polysiloxane component" to be crosslinked shall also be understood to cover copolymers with polysiloxanes having vinyl substituents or vinylterminated substituents.

For crosslinking, the amounts of the components are preferably selected so that the ratio of the molar amounts of the silicon hydrides to the double bonds is at least 1.

As stated above, the elastomer for use in this invention can be made by crosslinking one single fluorosubstituted siloxane-based polymer, or by crosslinking a mixture of a non-fluorosubstituted siloxane-based polymer and a fluoro-substituted siloxane-based polymer. The term "vinyl-functional polysiloxaue component" can thus be a mixture comprising a nonfluorosubstituted siloxane-based polymer and a fluorosubstituted siloxane-based polymer, where said polymer comprises 3,3,3-trifluoropropyl groups attached to the Si-atoms of the siloxane units. Alternatively, the "vinyl-functional polysiloxane component" can be a single fluoro-substituted siloxane-based polymer, where said polymer comprises 3,3,3-trifluoropropyl groups attached to the Si-atoms of the siloxane units.

Additionally, a so-called compatibiliser can be mixed with the abovementioned components. The compatibiliser is typically a block copolymer of a non-fluorosubstituted polymer and a fluorosubstituted polymer.

The silicon hydride-functional crosslinking agent is preferably a hydride-functional polysiloxane that may be straight chain, branched or cyclic. The hydride-functional siloxane crosslinking agent may also contain trifluoropropyl groups.

The fluorosubstituted siloxane-based polymer is preferably a PDMS polymer where approximately 50% of the methyl groups in said PDMS are replaced by 3,3,3-trifluoropropyl groups.

A filler, such as amorphous silica, is preferably added to the vinyl-functional component before the crosslinking.

In case the elastomer is made by crosslinking a polymer component in the presence of a peroxide catalyst, such a polymer component can be a mixture comprising a non-fluorosubstituted siloxane-based polymer and a fluorosubstituted siloxane-based polymer comprising 3,3,3-trifluoropropyl groups attached to the Si-atoms of the siloxane units. Alternatively, this polymer component can be a single fluorosubstituted siloxane-based polymer, where said polymer comprises 3,3,3-trifluoropropyl groups attached to the Si-atoms of the siloxane units.

The catalyst to be used in the crosslinking is preferably a noble metal catalyst, most commonly a platinum complex in alcohol, xylene, divinyl siloxane or cyclic vinyl siloxane. An especially suitable catalyst is a Pt(0)-divinyl-tetramethyl disiloxane complex.

Manufacture of the Implants

The implants according to this invention can be manufactured in accordance with standard techniques. The therapeutically active agent is mixed with the core matrix polymer, processed to the desired shape by molding, casting, extrusion, or other appropriate methods. The membrane layer can be applied onto the core according to known methods such as by mechanical stretching, swelling or dipping. Reference is made to the US-patents U.S. Pat. No. 3,832,252, U.S. Pat. No. 3,854,480, U.S. Pat. No. 4,957,119. An especially suitable method for preparation of the implants is disclosed in the Finnish patent FI 97947. This patent discloses an extrusion technology where prefabricated rods containing the active ingredient are coated by an outer membrane. Each such rod is, for example, followed by another rod without any active ingredient. The formed string is cut at the rods that contain no active agent. In this way, no special sealing of the ends of the implant is necessary.

Manufacture of the Intrauterine, Intravaginal and Intracervical Devices

The intra-uterine device can be made according to well known technology. a preferable intrauterine device (IUS, intrauterine system), intravaginal device or intracervical device in common use is a T-shaped body made of plastic material such as polyethene. The body consists of an elongate member (stem) having at one end a transverse member comprising two wings. The elongate member and the transverse member form a substantially T-shaped piece when the device is positioned in the uterus. The device has an attached thread long enough to protrude out of the cervical canal when the device is in position in the uterus. IUS:s releasing drugs have a drug reservoir adjusted around the elongate member. This drug reservoir is preferably a matrix which consists of the elastomer matrix with the active agent(s) dispersed therein. Preferably, the matrix is encased in a membrane. The membrane is usually made of an elastomer.

The drug reservoir adjusted around the stem of the T-shaped body can be manufactured as the implant as described above. Alternatively, the matrix can first be applied onto the step after which the matrix is encased by a membrane.

The matrix and membrane of the drug reservoir on the IUS can be made of the same elastomer as the implants described above.

EXPERIMENTAL SECTION

The invention is described below in greater detail in the following, non-limiting examples.

The intrauterine system (IUS) consisted of three parts: a core, a membrane and a body. The body was inert and its function was only minimal in a sense of controlling the release of the active agent. The core consisted of elastomer mixed with the active agent. The membrane was made from elastomer that controlled the release rate of the active agent.

The therapeutically active agent used in the examples was gestodene (GDN).

EXAMPLE 1

In this example 50% of the substituents of siloxane groups in the membrane were 3,3,3-trifluoropropyl groups.

Core Preparation 50 parts by weight GDN and 50 parts by weight of poly(dimethylsiloxane-co-vinylmethylsiloxane) and 1,2 parts by weight of dibentsoylperoxide-polydimethylsiloxane paste (50% of dichlorobenzoylperoxide) were mixed with a 2-roll mill. The mixture was extruded to a tube-like form with a wall thickness of 0,8 mm and outer diameter of 2,8 mm and cured by heat at +150° C. for 15 minutes, during which crosslinking took place. The cured (crosslinked) core was cut into 19 mm length.

Membrane Preparation 100 parts by weight of silica-filled poly (trifluoropropylmethylsiloxane-co-dimethylsiloxane-co-vinylmethylsiloxane) (content of trifluoropropyl-methylsiloxane units 99,7 mol %; i.e. degree of trifluoropropyl substitution 50%) and 1,2 parts by weight of dibentsoylperoxide-polydimethylsiloxane paste (50% of dichlorobenzoylperoxide) were mixed with a 2-roll mill. The mixture was extruded into a tube-like form with a wall thickness of 0,4 mm and cured by heat.

IUS Preparation 25 mm membranes and 19 mm cores were swelled with cyclohexane and placed into polyethene body of the IUS. Cyclohexane was allowed to evaporate.

Drug Release Test

The release rate of the drug from the implant was measured in vitro as follows:

the IUS were attached into a stainless steel holder in vertical position and the holders with the implants were placed into glass bottles containing 75 ml of a dissolution medium. The glass bottles were shaked in shaking waterbath 100 rpm at 37° C., The dissolution medium was withdrawn and replaced by a fresh dissolution medium at predetermined time intervals, and the released drug was analysed by HPLC. The concentration of the dissolution medium and the moment of change (withdrawal and replacement) of medium were selected so that sink-conditions were maintained during the test.

The results are shown in FIG. 1 as the daily in vitro release rate of gestodene.

EXAMPLE 2

In this example 18% of the substituents of siloxane groups in the membrane were 3,3,3-tifluoropropyl groups.

The core and the IUS were prepared according to the example 1.

Membrane Preparation 55 parts by weight of silica-filled poly (trifluoropropylmethylsiloxane-co-dimethylsiloxane-co-vinylmethylsiloxane) (content of trifluoropropyl-methylsiloxane units 99,7 mol-%), 45 parts by weight of silica-filled poly(dimethylsiloxane-co-vinylmethylsiloxane) (i.e.e degree of trifluoropropyl substitution 18%) and 1,2 parts by weight of dibentsoylperoxide-polydimethylsiloxane (50% of dichlorobenzoylperoxide) paste were mixed with a 2-roll mill. The mixture was extruded into a tube-like form with a wall thickness of 0,4 mm and cured by heat.

The dmg release test was performed according to example 1 and the results are shown in FIG. 1 as the daily in vitro release rate of gestodene.

Discussion of the Results

FIG. 1 shows the daily in vitro release rate of gestodene from the three IUS's according to examples 1 and 2. The square marked curve refers to example 1 and the triangle marked curve to example 2. The examples thus demonstrate clearly the retarding effect caused by the 3,3,3-trifluoropropyl substitution of the membrane polymer.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

What is claimed is:

1. A delivery device for the controlled release of the therapeutically active agent gestodene, over a prolonged period of time, at a release rate of 0,1–300 µg/day, said device comprising a core comprising at least said therapeutically active agent, and a membrane encasing said core wherein said membrane is made of an elastomer, characterised in that the elastomer is a siloxane-based elastomer comprising 3,3,3-trifluoropropyl groups attached to the Si-atoms of the siloxane units, and the release rate of said therapeutically active agent of said delivery device is regulated by the amount of said 3,3,3-trifluoropropyl groups.

2. The device according to claim 1, characterised in that it is an implant.

3. The device according to claim 2, characterised in that the release rate of the therapeutically active agent is 0,5–200 µg/day.

4. The device according to claim 1, characterised in that it is an intrauterine device.

5. The device according to claim 4, characterised in that the release rate of the therapeutically active agent is 0,5–100 µg/day.

6. The device according to claim 1, characterised in that it is an intravaginal device.

7. The device according to claim 1, characterised in that it is an intracervical device.

8. The device according to claim 1, characterised in that the elastomer is made of either I) a mixture comprising a) a non-fluorosubstituted siloxane-based polymer and b) a fluorosubstituted siloxane-based polymer, said polymner comprising 3,3, 3, -trifluoropropyl groups attached to the Si-atoms of the siloxane units, or II) a single siloxane-based polymer comprising 3,3,3-trifluoropropyl groups attached to the Si-atoms of the siloxane units, wherein said polymer or mixture of polymers are crosslinked to form the elastomer.

9. The device according to claim 8, characterised in that the mixture of polymers is a mixture of a) poly (dimethylsiloxane) and b) poly(dimethylsiloxane) in which the methyl groups attached to the Si-atoms of the siloxane units to some extent have been replaced by 3,3,3-trifluoropropyl groups.

10. The device according to claim 9, characterised in that approximately 50% of the methyl groups in the polymer b) have been replaced by 3,3,3-trifluoropropyl groups.

11. The device according to claim 1, characterised in that the elastomer contains a filler.

12. The device according to claim 11, characterised in that the filler is amorphous silica.

* * * * *